United States Patent [19]

Brandston et al.

[11] Patent Number: 5,047,006
[45] Date of Patent: Sep. 10, 1991

[54] PERSONAL INTEGRATING SPHERE SYSTEM

[76] Inventors: Howard Brandston, 141 W. 24th St., New York, N.Y. 10011; Aran Safir, 3 Ellsworth Ave., Cambridge, Mass. 02139

[21] Appl. No.: 432,782

[22] Filed: Nov. 6, 1989

[51] Int. Cl.$^5$ .................. A61G 10/100; A61G 10/02; A61M 21/100; A61B 1/06; A61N 00/00
[52] U.S. Cl. ........................................ 600/21; 600/27; 128/22; 128/395; 250/228
[58] Field of Search ....................... 600/21, 26, 27, 28, 600/25 A; 128/21, 22, 23, 24.1, 24.2, 745, 746, 380, 395, 396; 250/228, 215

[56] References Cited

U.S. PATENT DOCUMENTS

| | | | |
|---|---|---|---|
| 4,044,756 | 8/1977 | Hamilton et al. | 128/745 |
| 4,327,712 | 5/1982 | Frenkel et al. | 128/22 |
| 4,553,534 | 11/1985 | Stiegler | 600/28 |
| 4,853,542 | 8/1989 | Milosevic et al. | 250/228 |
| 4,858,609 | 8/1989 | Cole | 600/26 |

OTHER PUBLICATIONS

Article from Field Equipment catalog, p. 78.
Walsh, John W. T., Photometry (copyright 1958).
"Integrating Photometer", Van Nostrand's Scientific Encyclopedia, Fourth Edition, p. 925.
Boynton, Robert M., Human Color Vision (1979), pp. 15, 16, 17, 18 and 153-155.
"The Times of Your Life", Time Magazine (Jun. 5, 1989), pp. 66 and 67.
"Microlasers Offer New Reliability for R&D", Research & Development (Jun. 1989), pp. 72, 73 and 76.
"Society for Light Treatment and Biological Rhythms", SLTBR Newsletter (vol. 1, No. 2, Feb. 1989), pp. 1, 3, 5 and 9.
"Way Found to Reset Sleep Clock", Boston Globe, Friday, Jun. 16, 1989 (three articles).
"Optics and Vision Physiology", vol. 94, May 1976, pp. 852-862, from Archives of Ophthalmology.

*Primary Examiner*—Max Hindenburg
*Assistant Examiner*—Robin R. Longo

[57] ABSTRACT

A personal integrating sphere system that provides a field of illumination of substantially uniform intensity for beneficially affecting the mental and physical health of a user. The system includes an integrating sphere configured to permit the user to experience the field of illumination of substantially uniform intensity. The integrating sphere integrates illuminating light injected thereinto to provide uniform illumination within the sphere. The system also includes an illuminator that may be controlled by the user to provide illuminating light sequences of variegated hues and mixtures thereof, saturation, brightness and duration. A sound system may be used in combination with the integrating sphere system to enhance the effect of the illuminating light sequences.

17 Claims, 2 Drawing Sheets

PERSONAL INTEGRATING SPHERE SYSTEM

FIELD OF THE INVENTION

This invention relates generally to light devices, and more particularly to a personal integrating sphere system which provides a field of illumination of substantially uniform intensity for beneficially affecting the mental and physical health of the user.

BACKGROUND OF THE INVENTION

Medical evidence indicates that the mental and/or physical health of people may be affected by exposure to light. In particular, a condition know as seasonal affective disorder (SAD) has been recognized wherein certain individual depressive patients exhibit a periodic, yearly recurrence of their affective illness. These recurrences tend to occur during seasonal periods of low level and/or short duration light such as in late fall and winter. It has been discovered that the mental outlook of people exhibiting SAD symptoms, as well as non-seasonally depressed people, may be significantly improved by light therapy.

Light therapy involves exposure to light of predetermined intensities for predetermined periods of time. Exposure of the retinas to bright light stimulates the pineal body within the brain to regulate the production of melatonin, a mood-altering hormone. Preliminary clinical studies indicate that bright light of 2500 lux is effective in producing a marked remission rate in depressed persons. Bright light as low as 500–1000 lux and as high as 10,000 lux has also been shown to affect melatonin production. Differences in individual sensitivity affect the response to bright light. The duration of exposure is also a factor.

Generally, persons undergoing a regimen of light therapy have shown improvement within 2-4 days after commencement of therapy. While clinical studies have not established an optimal period of treatment, treatment periods of one to several weeks, with daily exposure periods that may extend over several hours, have generally been found to provide a significant remission rate. Treatment periods of such duration, however, when conducted in a clinical environment, are extremely inconvenient for the vast majority of the population. A need exists, therefore, for an apparatus that will allow people to undergo light therapy within their living environment, at their convenience.

In addition, most people experience affective stress levels in the conduct of their daily affairs. A need exists to provide conditions under which people can reduce the stress levels that may accumulate during the day. It has been recognized, however, that the human visual system automatically and continuously searches for patterns and dark-light boundaries within the visual field. Upon finding such patterns and/or dark-light boundaries, the brain works on a subconscious level to abstract meaning from such patterns and/or dark-light boundaries. This work occupies the brain to a great extent during waking hours.

This abstractive process may interfere with the reduction of stress levels. Therefore, a need also exists for a means for temporarily reducing or eliminating the abstractive process engendered by the human visual system. Meditation, which provides beneficial psychological and physical effects, may be one means of reducing the effects of the abstractive process. Light therapy under controlled conditions is another means of reducing the effects of the abstractive process.

It is also know that people's biological clocks may be disrupted due to the demands of their daily affairs. Disturbances in biological rhythms due to such conditions as jet lag, long working days, irregular work shifts or even such a mundane thing as sleeping late can have a detrimental effect on a person's efficiency and judgment. Recent experiments have shown that a regimen of light therapy, under controlled conditions, may be utilized to shift the sleep-wake cycle to alleviate disturbances in biological rhythms. A controlled light therapy regimen has also been shown to be useful in the treatment of sleep disorders.

SUMMARY OF THE INVENTION

A personal integrating sphere system is described that provides a field of illumination of substantially uniform intensity for beneficially affecting the mental and physical health of the user. The integrating sphere system has utility in providing a visual field of light of sufficient brightness for treatment of persons suffering from seasonal affective disorders and those affected by non-seasonal depression. The uniform intensity illumination provided within the integrating sphere by the integrating sphere system is also a featureless field of view, containing no patterns or dark-light boundaries, so that the human visual system and brain are not engaged in and burdened by the abstractive process. The uniform intensity illumination provided within the integrating sphere is also useful for resetting or modifying the sleep-wake cycle of people affected by disturbed biological rhythms or sleep disorders.

The personal integrating sphere system of the present invention includes an integrating sphere, which provides a featureless, uniformly illuminated field of view; an illuminator to provide a regulated light output of predetermined intensity, spectral composition, and duration; an optical coupler transmitting the illuminating light output of the illuminator to the integrating sphere; and a controller. The controller is operative to regulate the illuminating light output of the illuminator with respect to hue, saturation, brightness, and duration. The system may also include a microprocessor and a sound subsystem.

The integrating sphere of one embodiment is a hollow globe configured to receive therein the head of a user. The inner surface of the hollow globe is configured to integrate, by reflection and re-reflections in diverse directions, illuminating light injected thereinto to provide a featureless, uniformly illuminated visual field to the user.

The illuminator is a multi-channel light-generating device wherein each channel provides an illuminating light beam of predetermined hue and brightness. Illuminating light beams may be injected separately into the integrating sphere or mixed to provide additional hues in the integrating sphere. Each light-generating channel includes a light source providing radiant flux, a collimating lens, a filter for providing a predetermined hue from the radiant flux, and a user-adjustable modulating means for regulating the brightness of the light beam of predetermined hue. White light may be also generated by the illuminator to regulate the degree of saturation of the illuminating light. The illuminating light beams are introduced into the integrating sphere from the illuminator by means of an optical coupler.

A controller is provided so that the user may regulate the illuminating light beams with respect to hue, saturation, brightness and duration. A microprocessor may be used in combination with the integrating sphere system to record and/or store illuminating light sequences. The microprocessor may also be used to generate random illuminating light sequences. A sound system may be used in combination with the integrating sphere system to provide music with the illuminating light sequences. The temporal sequences of the illuminating light may be coordinated with the temporal sequences of sound via the microprocessor.

BRIEF DESCRIPTION OF THE DRAWINGS

A more complete understanding of the present invention and the attendant advantages and features thereof will be more readily understood by reference to the following detailed description when considered in conjunction with the accompanying drawings wherein.

DETAILED DESCRIPTION OF PREFERRED EMBODIMENTS

Figure 1:
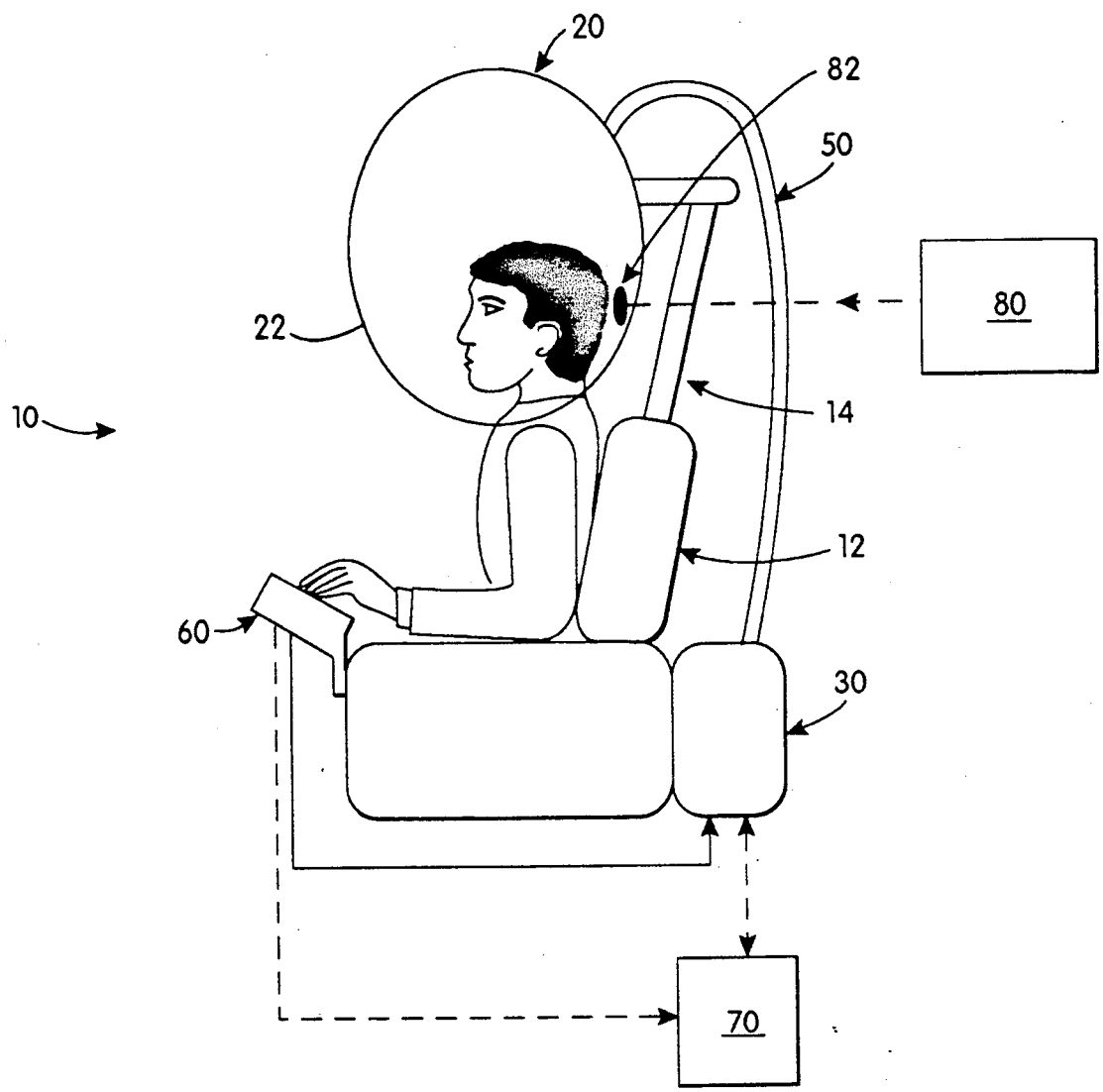
FIG. 1 illustrates an exemplary personal integrating sphere system according to the present invention.

Referring now to the drawings, wherein like reference numerals designate corresponding or similar elements throughout the several views, an exemplary embodiment of a personal integrating sphere system 10 according to the present invention is illustrated in FIG. 1. The personal integrating sphere system 10 includes an integrating sphere 20, which provides a featureless, uniformly illuminated field of view, an illuminator 30 to provide a regulated light output of predetermined intensity, spectral composition and duration, an optical coupler 50 transmitting the output of the illuminator 30 to the integrating sphere 20, and a controller 60. The controller 60 is operative to regulate the illuminating light output of the illuminator 30 with respect to hue, saturation, brightness and duration. The system 10 may also include a microprocessor 70 and a sound subsystem 80.

The personal integrating sphere system 10 is arranged to facilitate interaction therewith and operation thereof by one or more users. For the exemplary embodiment illustrated in FIG. 1, which is configured for a single user, the system 10 may be mounted in combination with a reclining chair 12. The integrating sphere 20 is mounted to the chair 12 by means of an adjustable support arm 14. The support arm 14 is adjustable to vary the height, forward, and rearward positions of the integrating sphere 20 with respect to the chair 12 so as to accommodate users of varying physical dimensions. The support arm 14 is also operative to swing the integrating sphere 20 upwardly away from the chair 12 so that the user may conveniently position himself in the chair 12.

The illuminator 30 may be conveniently mounted to the back of the chair 12. The controller 60 may be mounted on an arm of the chair 12 for user access. The disposition of the controller 60 allows the user to manually manipulate the output of the illuminator 30 as discussed in further detail hereinbelow. The controller 60 may also be used to control the output of the sound subsystem 80.

An integrating sphere is a well known device, which provides uniform illumination over a very large field of view, that is widely used by industry to measure luminous flux. The integrating sphere is a hollow sphere coated internally with a diffusing material, into which a source of light to be measured is placed, that operates on the principle that the luminance at any part of the internal surface due to diffusely reflected light from the remainder of the internal surface is proportional to the total flux emitted by the source.

Any object placed within an integrating sphere, as well as any imperfections or discontinuities in the diffusing material coating the internal surface, adversely effect the performance of the integrating sphere. Objects, imperfections, and discontinuities disturb the diffusion of the reflected flux and/or reduce the amount of the reflected flux, thereby reducing the efficacy of the integrating sphere for measuring luminous flux. Integrating spheres are therefore designed to minimize or compensate for internal objects, imperfections, and discontinuities which adversely effect measurement of luminous flux. For integrating spheres for industrial applications, one pragmatic approach for minimizing the negative effects of objects, imperfections, and discontinuities within the sphere is to construct spheres with large diameters.

Figure 2:
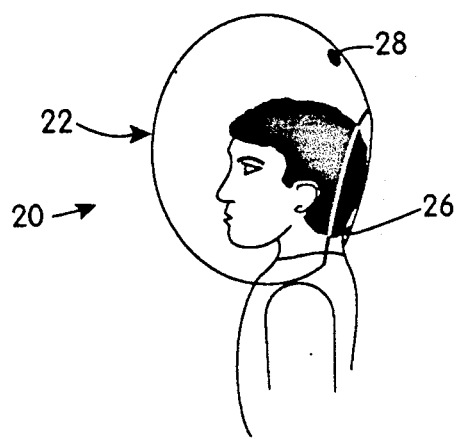
FIG. 2 is a plan view of a integrating sphere according to the present invention.

The integrating sphere 20 of the exemplary embodiment illustrated in FIG. 1 is a specialized adaption of the integrating sphere that is configured to receive the head of a single user as illustrated in FIG. 2. The integrating sphere 20 illustrated in FIG. 2 is shown as transparent for purposes of explication. It is to be understood that the integrating sphere 20 of the present invention is opaque when viewed externally.

The integrating sphere 20 is a hollow globe 22 having an inner surface 24 that is configured to diffusely reflect and re-reflect input light in random directions, i.e., the input light is "integrated" so that the inner surface is suffused with illumination of substantially uniform intensity. As exemplarily illustrated in FIG. 3, the inner surface 24 may be configured as a matte, or diffuse reflector.

The integrating sphere 20 illustrated in FIG. 2 also includes a head insertion aperture 26 and a light input port 28. The head insertion aperture 26 is configured so that the user may readily insert his head inside the hollow globe 22. The head insertion aperture 26 is formed at the bottom and rear portion of the hollow globe 22 such that the eyes of the user are directed towards an unbroken inner surface 24. The light input port 28 provides a means for injecting illuminating light onto the inner surface 24 of the hollow globe 22. In an alternative embodiment, the illuminating light may be routed into the interior of the hollow globe 22 via the head insertion aperture 26, thereby eliminating the need for a separate light input port. In another embodiment, the hollow globe 22 is divided into halves along a meridian and the halves are separable so that the user's head may be readily inserted inside the hollow globe 22, thereby eliminating the need for a head insertion aperture.

Figure 3:
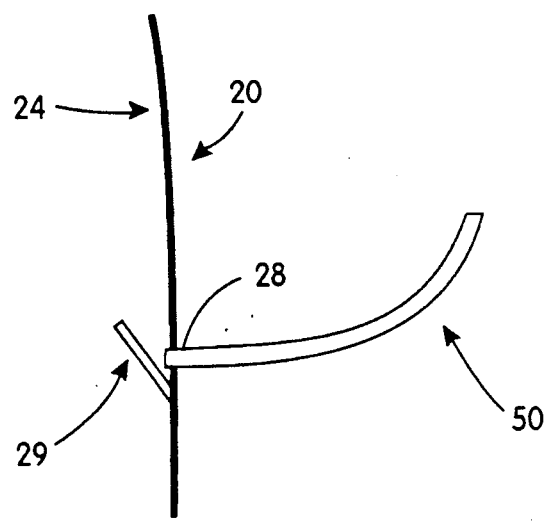
FIG. 3 is a partial cross-sectional view of the integrating sphere.

A small reflecting mirror 29 is mounted on the inner surface 2 of the hollow globe 22 adjacent the input end of the optical coupler 50. For the embodiment of the integrating sphere 20 illustrated in FIG. 2, the reflecting mirror 29 is mounted adjacent the input port 28 as shown in FIG. 3.

In designing the configuration of the integrating sphere 20 for use in the system 10 of the embodiment of FIG. 2, several operating constraints should be considered. The inner surface 24 of the hollow globe 22 should be spaced apart a sufficient distance from the head of the user to allow sufficient ventilation, to eliminate any sense of claustrophobia, to minimize any sensation of radiated body heat and to minimize any distracting auditory stimuli such as breathing or heartbeats.

There should be nothing in the user's visual field within the hollow globe 22 which would distract the user. A normal person has a field of view along the horizontal meridian (eye level) which is slightly greater than 180 degrees. The normal inferotemporal field of view, however, is large and may include portions of the thorax.

The inner surface 24 of the hollow globe 22 should be as spherical as possible. Deviations from sphericity, such as flattening, undesirably affect the reflecting function of the inner surface 24. In a similar manner, imperfections or discontinuities in the inner surface 24 detract from the generation of illumination with substantially uniform intensity.

As discussed hereinabove, the integrating sphere 20 illustrated in FIG. 2 includes the head insertion aperture 26, the light input port 28, and the reflecting mirror 29, which constitute imperfections/discontinuities of the inner surface 24. Pragmatically, however, the lack of sphericity resulting from these elements is not significant as their effects on the viewed illumination will not be noticeable to the occupant of the sphere inasmuch as the human visual system easily adapts to the limiting effects caused by these elements.

The preferred medial diameter of the single occupant integrating sphere 20 illustrated in FIG. 2 should be within the range of 14–18 inches (35–45 cm). The diameter range was based upon head dimensions arranged by percentiles for the population. Such information is presented in The Measure of Man; Human Factors in Design, by Henry Dreyfuss. The archetypical user has a head dimension, from the tip of the nose to the farthest posterior point (occiput) of about 9.5 inches (24 cm). The lower margin of the integrating sphere 20 should be disposed under the chin of the user and adjacent thereto and above the shoulders of the user.

The sizing and disposition as discussed hereinabove ensures that user's field of vision encompasses only the inner surface 24 of the hollow globe 22. Accordingly, for the embodiment of the integrating sphere 20 illustrated in FIG. 2, no visual distractions such as the user's thorax are within the visual field within the hollow globe 22. It is to be understood, however, that the personal integrating sphere system 10 according to the present invention is not limited to the embodiment hereinabove described.

For example, another embodiment of the integrating sphere 20 may have a medial diameter of 24 inches (61 cm), thereby providing a greater distance between the occupant's eyes and the inner surface 24. With a sphere 20 of such diameter and the occupant's eyes on the medial plane, the lower edge of the hollow globe 22 encompasses a portion of the user's thorax. Concomitantly, however, the area of the inner surface 24 has been increased to provide a greater diffusion capability such that the user experiences a field of illumination of substantially uniform intensity.

It will be appreciated that integrating spheres having a medial diameter that would permit one or more occupants to be situated completely within the integrating sphere are within the scope of the present invention. Such integrating spheres should be sized so that the obstructing effects resulting from the one or more occupants are compensated for by the increased diffusion capability of the increased area of the inner surface such that the visual system of the one or more occupants experiences a field of illumination of substantially uniform intensity. Such large sized integrating spheres may be fabricated to divide into two parts along a meridian, the parts being separable to permit easy ingress and egress of the one or more users.

The illuminator 30 of the instant invention is operative to provide one or more light beams of high spectral purity and predetermined brightness or intensity. One embodiment of the personal integrating sphere system 10 of the instant invention is operative for its intended purpose utilizing a single channel illuminator 30 that provides a single light beam of predetermined intensity. The single light beam may have a predetermined hue, as discussed hereinbelow, or may be white light. The single light beam is "integrated" by the integrating sphere 20 to provide featureless light of the predetermined hue and uniform intensity over the inner surface 24 of the hollow globe 22. It has been determined, however, that the utility of the present invention is greatly enhanced by utilizing an illuminator 30 that is capable of providing several hues.

Any hue or color visible to the human eye can be created by the proper mixture of three "primary" hues of the color spectrum. The three primary hues are red, green, and blue. White light may be utilized to obtain various degrees of saturation.

Another embodiment of the illuminator 30 of the instant invention is a multi-channel light generating device that is capable of producing illuminating light beams for the integrating sphere 20 of various hues of monochromatic light and white light. The illuminator 30 may also be configured to provide illuminating beams at other wavelengths.

A preferred embodiment of the multi-channel light-generating device 30 according to the present invention includes four light-generating channels 32. Three of the light-generating channels 32 are utilized to generate the three primary hues of red, green, and blue. The fourth light-generating channel 32 is utilized to generate white light for regulating saturation.

The multi-channel light-generating device 30 should produce illuminating light beams having a luminance sufficient to provide therapeutic benefits consonant with the particular application. By way of example only, illuminating light beams having luminance within the range of 500 to 10,000 lux have been demonstrated to provide therapeutic benefits in certain applications, as discussed hereinabove.

Figure 4:
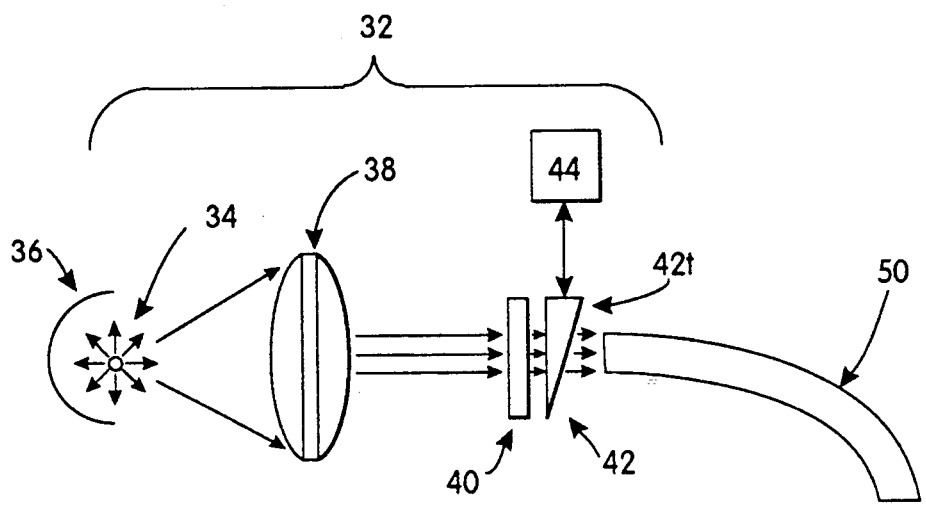
FIG. 4 is a schematic view of one channel of an illuminator according to the present invention.

An exemplary light-generating channel 32 of the illuminator 30, for generating an illuminating light having a predetermined hue of predetermined brightness, is illustrated in FIG. 4. The channel 32 includes a light source 34, a back reflector 36, a collimating lens 38, an interference filter 40, a neutral density wedge 42 and a means 44 coupled to the neutral density wedge 42 for displacement thereof.

For low cost commercial applications, the light source 34 may be a 500 watt halogen/tungsten projector lamp such as the type used in motion picture or 35 mm slide projectors. Such lamps are conveniently powered from an ordinary 110 volt, 15 amp line. For applications where cost is not a primary consideration, a high power xenon arc, which has good emission characteristics at short wavelengths as well as the rest of the spectrum, may be used.

The back reflector 36 focuses the radiant flux generated by the light source 34 onto the collimating lens 38. The collimating lens 38 collimates the radiant flux and directs it through the interference filter 40. The interference filter 40 suppresses all wavelengths of the radiant flux except for a narrow band of wavelength corresponding to the predetermined hue.

Equal amounts of radiant flux of different wavelengths do not produce visual sensations of equal brightness. Therefore, the illuminator 30 provides light filtering that modulates the intensity of the light beam of predetermined hue without changing the relative spectral energy distribution of the hue. Light intensity modulation is effected by the neutral density wedge 42. Coupled to the neutral density wedge 42 is the displacement means 44 that allows relative movement of the wedge with respect to the light beam to vary the modulating effect, and thereby provide an illuminating light beam of predetermined hue and brightness.

The thick end 42t of the neutral density wedge 42 may be configured to act as an optical shutter by making the end totally opaque. This enhances the utility of the illuminator 30 inasmuch as one or more light generating channels 32 may be effectively blocked off so that mixing of hues may be varied in dependence upon the particular application.

Other means may be used to generate illuminating light beams of predetermined hue, predetermined brightness, and high spectral purity. The illuminator 30 may comprise one or more lasers, e.g., gas-discharge lasers such as helium-neon, helium-cadmium, carbon dioxide, and argon-ion, or solid-state lasers such as yttrium-aluminum-garnet and yttrium-lithium fluoride, each of which provides radiation of predetermined wavelength. Of particular interest are microlasers, a new class of miniaturized, all-solid state laser devices of high stability, low noise, and high beam quality. Microlasers have been developed that generate radiation at green, red,, and blue wavelengths.

The optical coupler 50, which is optically interfaced with each light generating channel 32 of the illuminator 30 and the light input port 28, is operative to transmit illuminating light beams to the integrating sphere 20. The optical coupler 50 may be a fiber optic bundle. Illuminating light beams emerging from the fiber optic bundle are directed onto the reflecting mirror 29 and reflected therefrom onto the inner surface 24 of the hollow globe 22 for integration. Preferably, the reflecting mirror 29 is positioned so that the illuminating light beams are initially reflected onto the inner surface 24 outside of the visual field of the user, such as on the inner surface 24 above the user's head.

For those embodiments of the present invention wherein the multi-channel light-generating device 30 is operative to provide more than one primary hue of predetermined brightness, the generated primary hues must be combined or mixed at some point within the system to provide the full range of hues possible. One means of accomplishing this is by utilizing a fiber optic bundle 50 which is divided into sub-bundles 50x, each sub-bundle 50x being associated with a respective light-generating channel 32 and dedicated to the transmission of the primary hue generated within the respective channel 32. For this particular embodiment, mixing would occur after the individual hues were reflected onto the inner surface 24 of the integrating sphere 20.

The controller 60 is coupled to the illuminator 30. The controller 60 is operative to allow the user to regulate the parameters, i.e., hue, brightness, saturation, and duration, of each light-generating channel 32 so that the user may control the uniform illumination generated within the integrating sphere 20. The switches of the controller 60 may be configured for identification by their shapes so that the user may operate the controller 60 by tactile impressions.

A microprocessor 70 may be used in combination with the personal integrating sphere system 10 as described hereinabove. The microprocessor 70 may be operated under the control of the user via the controller 60, or may operate autonomously, or both. The microprocessor 70 may be used to record and/or store illuminating light sequences generated by the illuminator 30. Illuminating light sequences may be stored on portable memory devices such as magnetic disks which would facilitate exchanges of illuminating light sequences between different users. The microprocessor 70 may be operative to generate random illuminating light sequences via a random mode generator. Random illuminating light sequences may be recorded and/or stored.

A sound system 80 may also be used in combination with the personal integrating sphere system 10 as described hereinabove. Small, wide-range speakers 82 may be embedded within the wall of the hollow globe 22 outside of the visual field of the user, such as in proximity to the user's ears, as shown in FIG. 1. The sound generated by the sound system 80 may be independent of the illuminating light sequences or alternatively may be synchronized therewith. Illuminating light sequences may have a rhythm matched to the rhythm of the sound. In another embodiment, the microprocessor 70 may be used in combination with the sound system 80 to simultaneously synthesize sound and illuminating light sequences.

A variety of modifications and variations of the present invention are possible in light of the above teachings. It is, therefore, to be understood, that within the scope of the appended claims, the present invention may be practiced otherwise than as specifically described hereinabove.

What is claimed is:

1. A personal integrating sphere system for beneficially affecting the mental and physical health of a user, comprising:

illuminator means for generating at least one illuminating light beam of predetermined hue, saturation, brightness, and duration;

integrating sphere means having an internal configuration for diffusely reflecting and re-reflecting said at least one illuminating light beam to integrate said at least one illuminating light beam to provide a uniform, featureless illuminated field of view of substantially uniform intensity within said integrating sphere means, said internal configuration of said integrating sphere means being configured to accommodate at least the head of the user internally within said integrating sphere means in such manner that the user visually experiences said uniform, featureless illuminated field of view of substantially uniform intensity; and coupler means for optically coupling said at least one illuminating light beam from said illuminator means to said integrating sphere means wherein said at least one illuminating light beam is initially injected onto said internal configuration of said integrating sphere means outside the visual field of the user.

2. The personal integrating sphere system of claim 1 wherein said illuminator means comprises light-generating channel means for generating said at least one illuminating light beam having a predetermined hue of predetermined brightness, and wherein said coupler means is operative to optically couple said at least one illuminating light beam into said integrating sphere means by initially injecting said at least one illuminating sphere beam onto said internal configuration of said integrating sphere means outside the visual field of view of the user, and wherein said internal configuration of said integrating sphere means diffusely reflects and re-reflects said at least one illuminating light beam to integrate said at least one illuminating light beam to provide said uniform, featureless illuminated field of view of substantially uniform intensity having said predetermined hue within said integrating sphere means.

3. The personal integrating sphere system of claim 2 wherein said light-generating channel means is operative to generate a first illuminating light beam having a first predetermined hue of predetermined brightness and a second illuminating light beam having a second predetermined hue, and wherein said coupler means is operative to optically couple said first and second illuminating light beams into said integrating sphere means onto said internal configuration of said integrating sphere means outside the visual field of view of the user, and wherein said internal configuration of said integrating sphere means diffusely reflects and re-reflects said first and second illuminating light beams to said first and second illuminating light beams to provide said uniform, featureless illuminated field of view of substantially uniform intensity having a hue corresponding to a mixture of said first and second predetermined hues within said integrating sphere means.

4. The personal integrating sphere system of claim 3 wherein said light-generating channel means includes means for generating white light to regulate saturation of said first and second illuminating light beams.

5. The personal integrating sphere system of claim 2 wherein said light generating channel means is operative to generate a first illuminating light beam having a first predetermined hue of predetermined brightness, a second illuminating light beam having a second predetermined hue of third illuminating light beam having a third predetermined hue of predetermined brightness, and wherein said coupler means is operative to optically couple said first, second and third illuminating light beams into said integrating sphere means onto said internal configuration of said integrating sphere means outside the visual field of view of the user, and wherein said internal configuration of said integrating sphere means diffusely reflects and re-reflects said first, second and third illuminating light beams to integrate said first, second and third illuminating light beams to provide said uniform, featureless illuminated field of view of substantially uniform intensity having a hue corresponding to a mixture of said first, second and third predetermined hues within said integrating sphere means.

6. The personal integrating sphere system of claim 5 wherein said light-generating channel means includes means for generating white light to regulate saturation of said first, second and third illuminating light beams.

7. The personal integrating sphere system of claim 2 wherein said light-generating channel means includes means for generating white light to regulate saturation of said at least one illuminating light beam.

8. The personal integrating sphere system of claim 2 wherein said light-generating channel means comprises:
at least one light-generating channel for producing said at least one illuminating light beam having said predetermined hue of predetermined brightness, said at least one light-generating channel including light source means for generating radiant flux;
lens means for collimating said radiant flux;
filter means for producing a light beam having said predetermined hue by suppressing all wavelengths of said radiant flux except a narrow band of wavelength corresponding to said predetermined hue; and
means for modulating the intensity of said light beam having said predetermined hue to provide said at least one illuminating light beam having said predetermined hue of said predetermined brightness.

9. The personal integrating sphere system of claim 8 wherein said modulating means includes opaque means for blocking said light beam having said predetermined hue wherein said at least one light-generating channel produces no illuminating light beam.

10. The personal integrating sphere system of claim 2 further comprising controller means coupled to said light-generating channel means and adjustable by the user for regulating hue, brightness, saturation and duration of said at least one illuminating light beam.

11. The personal integrating sphere system of claim 2 further comprising microprocessor means coupled to said light-generating channel means for storing and recording sequences of said at least one illuminating light beam coupled to said integrating sphere means.

12. The personal integrating sphere system of claim 11 wherein said microprocessor means is further operative for randomly generating sequences of said at least one illuminating light beam.

13. The personal integrating sphere system of claim 2 further comprising sound system means coupled to said integrating sphere means for generating sound in conjunction with said at least one illuminating light beam within said integrated sphere means.

14. The personal integrating sphere system of claim 13 further comprising microprocessor means coupled to said light-generating channel means and said sound system means for simultaneously synthesizing sound and said at least one illuminating light beam.

15. The personal integrating sphere system of claim 1 wherein said integrating sphere means comprises a hollow globe having said internal configuration sized to receive at least the head of the user therein, said internal configuration of said hollow globe having an inner surface configured to provide multiple diffuse reflections and re-reflections in multiple directions of said at least one illuminating light beam to provide said uniform, featureless illuminated field of view of substantially uniform intensity within said hollow glove and an insertion aperture configured to permit at least the head of the user to be inserted within said hollow globe.

16. The personal integrating sphere system of claim 15 wherein said hollow globe has a light input port formed therethrough for interfacing said coupler means to said hollow globe wherein said at lest one illuminating light beam is injected into said hollow globe onto said inner surface configured to diffusely reflect and re-reflect in multiple direction said at least one illuminating light beam outside the visual field of view of the user and diffusely reflected and re-reflected from said inner surface thereof to form said uniform, featureless illuminated field of view of substantially uniform intensity.

17. The personal integrating sphere system of claim 16 further comprising a small reflecting mirror affixed to said inner surface of said hollow globe in proximity to said light input port wherein said at least illuminating light beam is reflected from said small reflecting mirror onto said inner surface of said hollow glove outside the visual field of the user and diffusely reflected and re-reflected therefrom to form said uniform, featureless illuminated field of view of substantially uniform intensity.

* * * * *

UNITED STATES PATENT AND TRADEMARK OFFICE
CERTIFICATE OF CORRECTION

PATENT NO. : 5,047,006
DATED : September 10, 1991
INVENTOR(S) : Howard Brandston, et al It is certified that error appears in the above-indentified patent and that said Letters Patent is hereby corrected as shown below:

On cover page before the heading "ABSTRACT" insert --Attorney, Agent, or Firm - Weingarten, Schurgin, Gagnebin & Hayes--.

Column 4, line 64, "surface 2" should read --surface 24--.

Column 9, line 45, "light generating" should read --light-generating--.

Column 11, line 2, "multiple direction" should read --multiple directions--.

Column 12, line 4, "hollow glove" should read --hollow globe--.

Signed and Sealed this

Fourth Day of January, 1994

Attest:

BRUCE LEHMAN

*Attesting Officer*   Commissioner of Patents and Trademarks